United States Patent [19]

Marcus

[11] Patent Number: 4,637,400
[45] Date of Patent: Jan. 20, 1987

[54] FOR CHARACTERIZING A HEART CONDITION

[76] Inventor: Edward N. Marcus, 49 Fiske Rd., Wellesley, Mass. 02181

[21] Appl. No.: 765,373

[22] Filed: Aug. 13, 1985

Related U.S. Application Data

[63] Continuation-in-part of Ser. No. 702,131, Feb. 15, 1985, abandoned.

[51] Int. Cl.$^4$ .............................................. A61B 5/00
[52] U.S. Cl. ...................................... 128/653; 128/695
[58] Field of Search ............... 128/630, 653, 695, 696, 128/713, 699

[56] References Cited

U.S. PATENT DOCUMENTS

| | | | |
|---|---|---|---|
| 3,811,040 | 5/1974 | Weinfurt et al. | 128/699 |
| 3,980,076 | 9/1976 | Wikswo, Jr. et al. | 128/713 |
| 4,101,961 | 7/1978 | Reiber | 128/695 |

FOREIGN PATENT DOCUMENTS 2447396  4/1976  Fed. Rep. of Germany ...... 128/695

OTHER PUBLICATIONS

Kaneko et al, "Straight-Line Approximation for the Boundary of the Left Ventricular Chamber from a Cardiac Cineangiogram", IEEE Transactions on Biomedical Engineering, vol. BME-20, No. 6, Nov. 1973, pp. 413–416.

Santamore et al, "A Comparative Study of Various Single-Plane Cineangiocardiographic Methods to Measure Left Ventricular Volume", IEEE Transactions on Biomedical Engineering, vol. BME-20, No. 6, Nov. 1973, pp. 417–421.

Primary Examiner—Kyle L. Howell
Assistant Examiner—Ruth S. Smith
Attorney, Agent, or Firm—Charles Hieken

[57] ABSTRACT

A heart is medically imaged to provide outlines of the end systole, mid systole and end diastole images of the heart. There is provided for each outline a sequence of functional relationships for the normalized curvature of a point to the normalized distance along the outline from the apex of each outline to provide a normalized curvature distribution function for each outline that are differentially combined to provide a normalized curvature difference function that is displayed. The latter is compared with a normal average normalized curvature difference function representative of normal hearts to evaluate the heart condition.

2 Claims, 12 Drawing Figures

FOR CHARACTERIZING A HEART CONDITION

This application is a continuation-in-part of pending application Ser. No. 702,131 filed Feb. 15, 1985, now abandoned.

The present invention relates in general to curve analysis and more particularly concerns novel techniques for analyzing shapes in two-dimensional images of the heart. These techniques are helpful in determining a numerical representation of heart abnormalities.

One approach to diagnosis of cardiac impairment involves obtaining an image of the heart through X-ray, ultrasonic or other suitable medical imaging techniques. Shapes typically of interest are the end diastole (heart fully expanded), end systole (heart fully contracted), and mid systole (heart partially contracted) shapes of the heart. Typical prior techniques characterize these shapes by the displacement of their outlines from a reference axis or reference point; that is, the relative displacement of corresponding points on the outlines of one or more shapes from a common reference axis or reference point. These techniques have limited accuracy and require realignment of shapes to a common reference axis or reference point for shape comparison.

The following references were published prior to the filing date of the parent of this application. 1. Azancot, A., Caudell, T., Allen, H., Horowitz, S., Sahn, D., Stoll, C., Thies, C., Valdes-Cruz, L., Goldberg, S.: Analysis of ventricular shape by echocardiography in normal fetuses, newborns and infants. Circulation 68: 1201, 1983. 2. Iizuki, M., Ohya, F., Otani, Y., Serizawa, T., Sugimoto, T.: Curvature distribution along the border of left ventricularogram to characterize left ventricular shape. VIth Inter. Conf. of Cardio. Vasc. System Dynamics Soc., Phila. Pa., 1984.

According to the invention, there is provided a curve such as a two-dimensional outline of the shape to be characterized according to the invention. The normalized curvature of a sequence of points distributed along the outline of the curve is determined progressively from one point to the next for all points on the curve. Normalized curvature at a point on a curve corresponds to the curvature at that point multiplied by a predetermined pathlength of the curve (such as the outline perimeter) and divided by $2\pi$. The curvature at a point along a curve is the rate of change of the curve's tangential angle as measured along the curve pathlength at the position of the point. Curvature may be manually determined by well-known graphical techniques or with well-known computer techniques which typically display the outline on a cathode ray tube and determine curvature by well-known techniques which employ computer software. Normalized curvature values which are obtained in this way are then preferably provided as a function of pathlength position to obtain a Normalized Curvature Distribution. This distribution may be provided manually by plotting the normalized curvature of each point as a function of pathlength position on the curve. Alternatively and preferably, the normalized curvature distribution is provided on a cathode ray tube screen or other graphical display with the assistance of a computer using well-known techniques.

In a specific application of the invention for analyzing a particular heart, the heart is medically imaged to provide end diastolic, end systolic, and/or mid systolic outlines, and the end diastolic outline, the end systolic, and mid systolic outlines are processed as set forth above to provide an end diastolic normalized curvature distribution, an end systolic normalized curvature distribution and mid systolic normalized curvature distributions. The end diastolic, end systolic and mid systolic normalized curvature distributions are then differentially combined to provide Normalized Curvature Difference Functions that characterize the particular heart whose end diastolic, end systolic and mid systolic outlines have been thus processed. This differential combining may be practiced manually by graphically subtracting on a point by point basis, the value of one normalized curvature distribution from the value of another normalized curvature distribution at corresponding pathlength positions and plotting the difference. Alternatively and preferably, differential combining of two normalized curvature distributions is performed by a computer that may display the Normalized Curvature Difference Functions on a cathode ray tube screen or print them out with a graphical printer.

Numerous other features, objects and advantages of the invention will become apparent from the following specification when read in connection with the accompanying drawing in which.

Figure 1A:
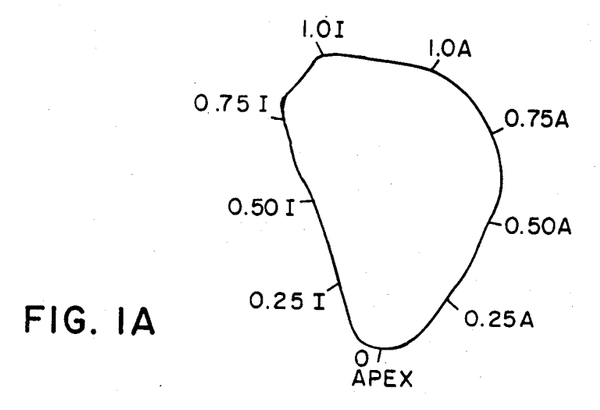
FIG. 1A shows a typical cardiac outline.

With reference now to the drawings and more particularly FIG. 1A thereof, there is shown a two-dimensional outline with marks designated as the apex, 0.25 A, 0.50 A, 0.75 A, 1.0 A, 0.25 I, 0.50 I, 0.75 I, and 1.0 I. The point 1.0 A is the intersection of the anterior wall with the aorta. The points 0.25 A, 0.50 A, and 0.75 A represent percentages of distance measured along the pathlength from the apex to the point 1.0 A. The point 1.0 I is the right hand edge of the mitral valve where the mitral valve intersects with the aorta. The points 0.25 I, 0.50 I, and 0.75 I represent percentages of distance measured along the pathlength from the apex to the point 1.0 I.

Figure 1B:
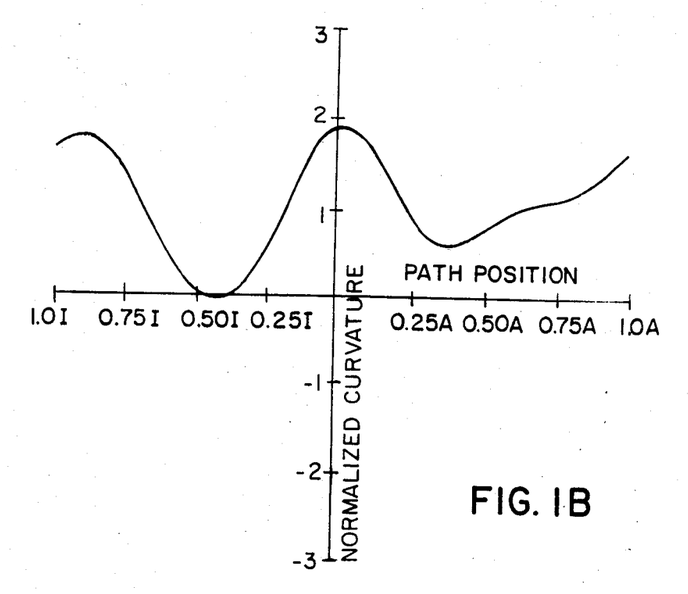
FIG. 1B is a graphical representation of normalized curvature as a function of pathlength position for the outline of FIG. 1A.

Referring to FIG. 1B, there is shown a graphical representation of the normalized curvature of the outline of FIG. 1A as a function of pathlength position. The curvature is the rate of change of the tangential angle with pathlength. Stated mathematically, and calling the tangential angle at a point a(x) where "x" is the distance measured along the path outline to the point in a counterclockwise direction from the apex, and "r" is the radius of curvature at the point, curvature=1/r(x)=da(x)/dx. This normalized curvature as a function of pathlength position in FIG. 1B characterizes the shape of the outline of FIG. 1A.

Figure 2A:
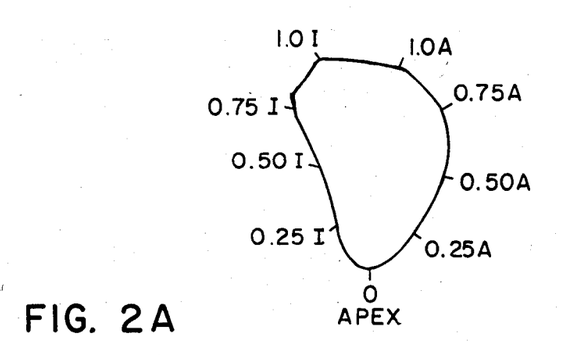
FIG. 2A is an outline of the same shape as the outline of FIG. 1A but of smaller size.
Figure 2B:
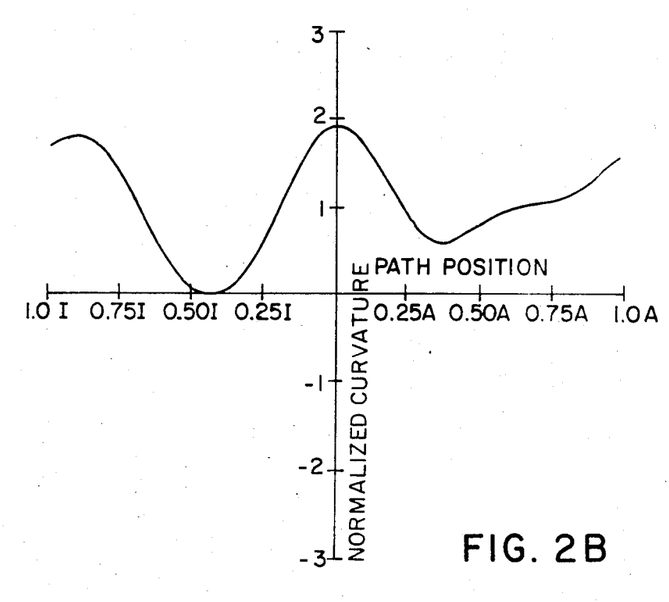
FIG. 2B is the normalized curvature as a function of pathlength position for the outline of FIG. 2A.

Referring to FIG. 2A, there is shown an outline having the same shape as that of FIG. 1A, but significantly smaller. FIG. 2B is a graphical representation of the normalized curvature of the outline of FIG. 2A as a function of pathlength position that is the same as the graphical representation of FIG. 1B. Thus normalized curvature as a function of pathlength position characterizes outline shape independently of outline size.

Figure 3A:
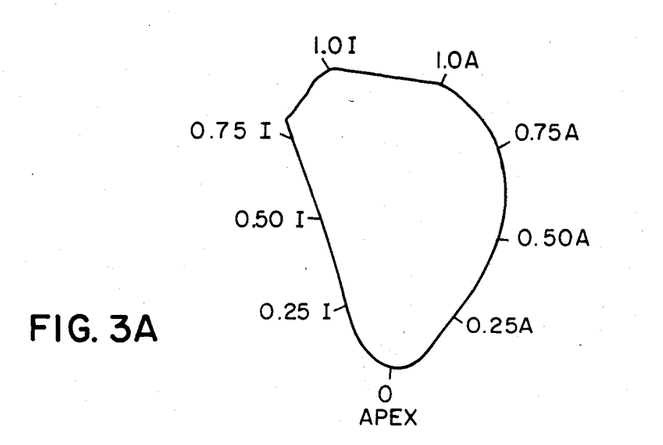
FIG. 3A is the outline of an image at end diastole.

Referring to FIG. 3A there is shown the outline of an end diastole image of a heart fully expanded and typically obtained from an X-ray, ultrasonic or other suitable medical imaging technique. The reference point is preferably the apex or the tip of the left ventricle designated in FIG. 3A. The apex value of pathlength position is zero. As the path of the outline is traversed in a counterclockwise direction from the apex, the value of the pathlength position increases until the point 1.0 A is reached where the anterior wall intersects the aorta. As the path of the outline is traversed in a clockwise direction from the apex, the value of pathlength position increases until the point 1 is reached at the intersection of the mitral valve with the aorta.

Figure 3B:
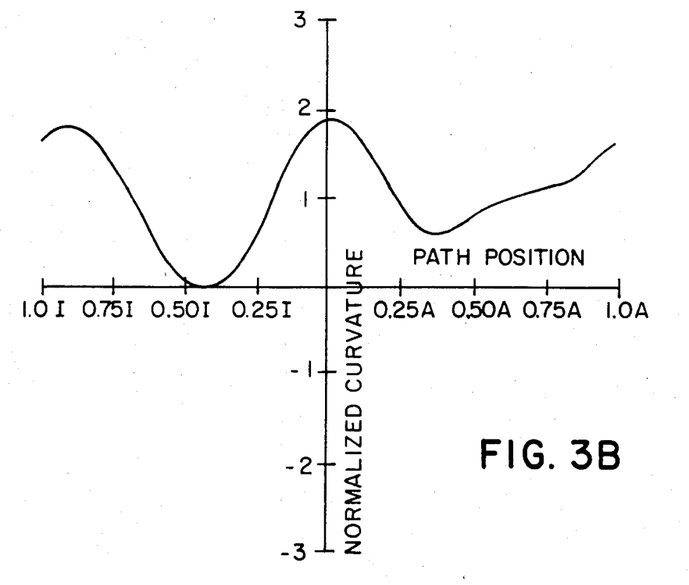
FIG. 3B is a graphical representation of the normalized curvature as a function of pathlength position for the outline of FIG. 3A.

Referring to FIG. 3B, there is shown a graphical representation of the normalized curvature of the outline of the end diastole image as a function of pathlength position.

Figure 4A:
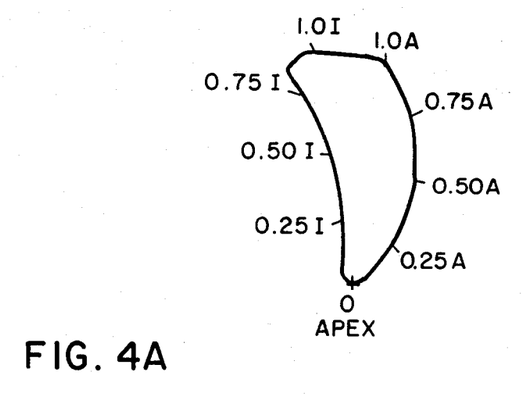
FIG. 4A is an outline of the image of the end systole of the same heart represented by the end diastole outline of FIG. 3A.
Figure 4B:
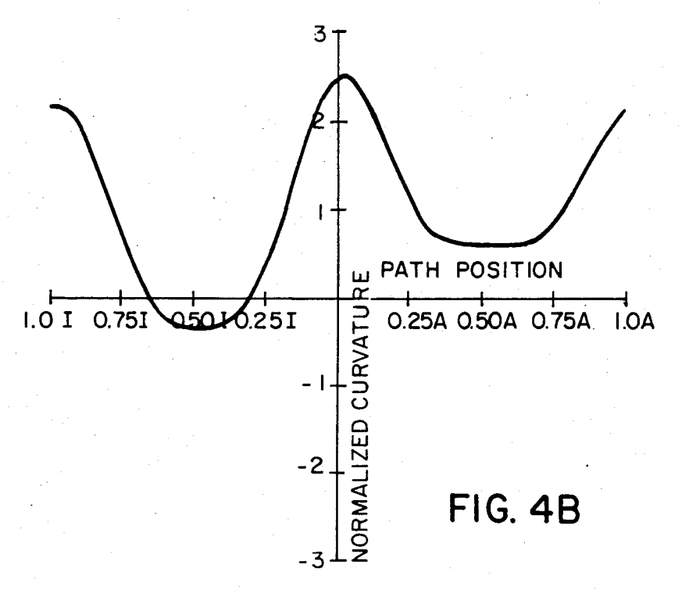
FIG. 4B is a graphical representation of normalized curvature as a function of pathlength position for the outline of FIG. 4A.

Referring to FIG. 4A, there is shown an outline of the end systole image for the same heart whose end diastole image outline is shown in FIG. 3A, but now fully contracted. Referring to FIG. 4B, there is shown a graphical representation of the normalized curvature of the end systole image outline of FIG. 4A as a function of pathlength position.

Figure 5A:
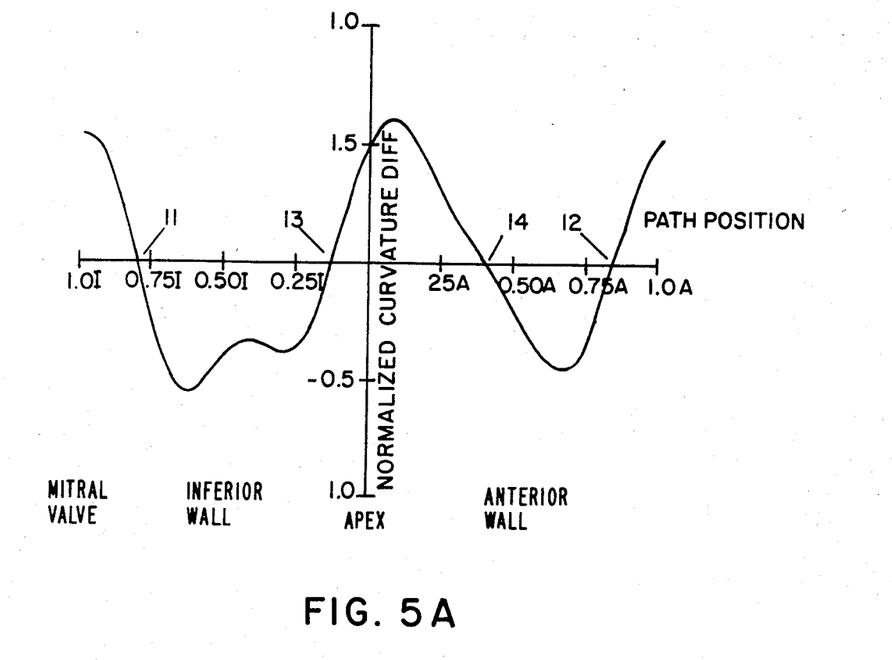
FIG. 5A is a graphical representation of the end diastole-end systole normalized curvature difference as a function of pathlength position for the heart whose end diastole and end systole outlines are shown in FIGS. 3A and 4A formed by differentially combining the graphical representations in FIGS. 3B and 4B.

Since the normalized curvature characterizes shape independently of size, the difference between the normalized curvature of the end diastole image outline of FIG. 3B and the end systole image outline of FIG. 4B is characteristic of the difference of shape between the outlines of FIGS. 3A and 4A. Referring to FIG. 5A, there is shown a graphical representation of this difference denoted as the normalized curvature difference as a function of pathlength position. This normalized curvature difference has values characterizing contraction properties of left ventricle wall regions. Thus, the region embracing the apex characterizes the apical region of the left ventricle and extends between the two zero crossings 13 and 14 embracing the apex, the portion characterizing the anterior wall region extends between zero crossings 14 and 12, the portion characterizing the inferior wall extends between the crossings 11 and 13, the portion characterizing the mitral valve region extends from the value 1.0 I of pathlength position to the zero crossing 11, and the portion characterizing the region of intersection between the anterior wall and the aorta extends from zero crossing 12 to the pathlength position 1.0 A. It will be obvious to those skilled in the art, that alternative methods of specifying pathlength position may be employed and that a complete enclosure of the LV outline may be used to include analysis by the invention of the aortic valve regions of the ventricle by similar methods of normalized curvature difference.

Figure 5B:
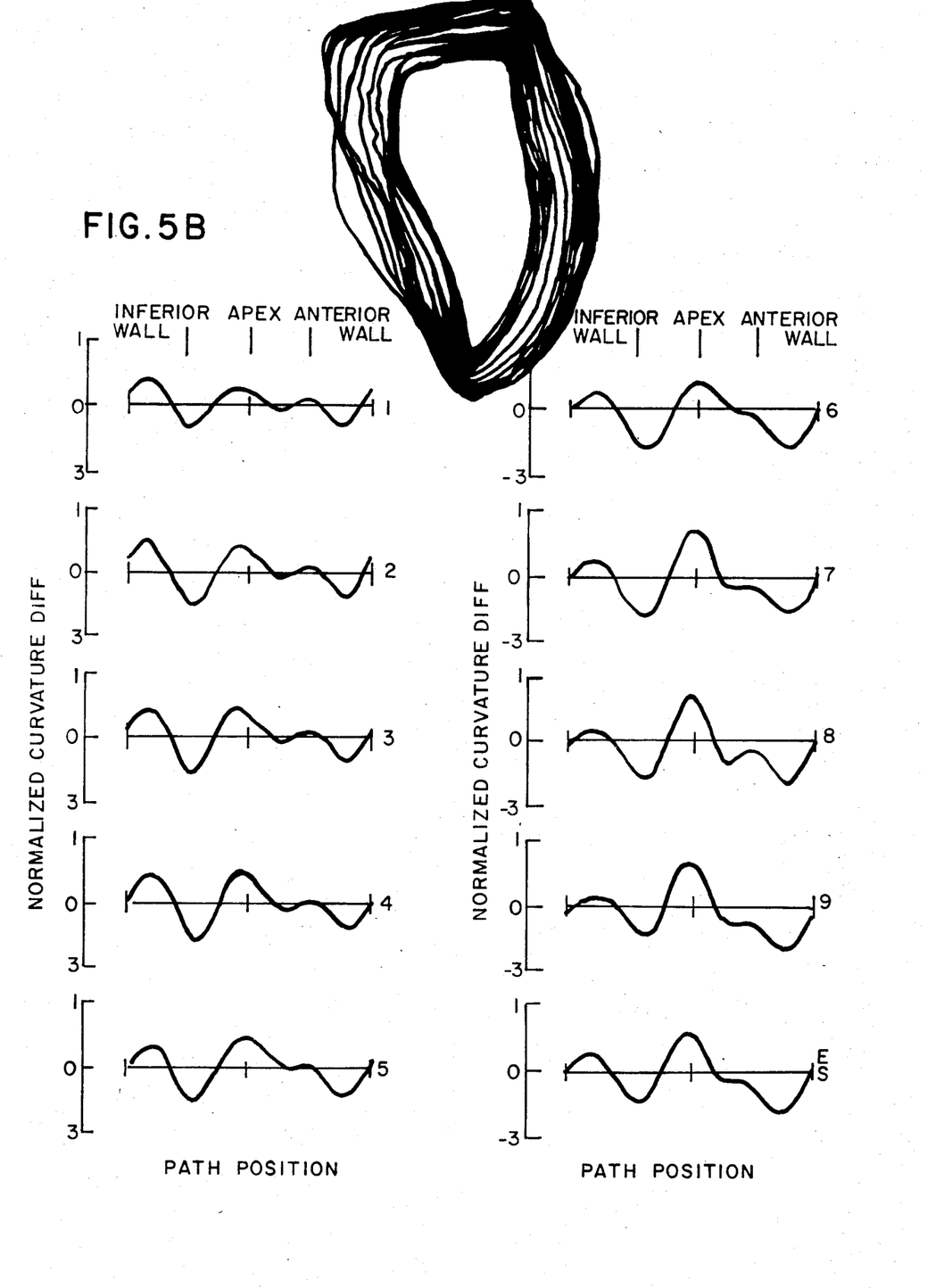
FIG. 5B is a graphical representation of the normalized curvature difference as a function of pathlength position for a sequence of consecutive systolic outlines for the heart shown at the top of the figure.

Referring to FIG. 5B, there is shown a sequence of Normalized Curvature Difference Functions obtained by differentially combining normalized curvature values from mid systolic outlines with corresponding normalized curvature values at end diastole. Sequential normalized curvature functions provide diagnostic information of left ventricle shape changes over small intervals of time during systole. Clinical experience with sequential NCDF functions has demonstrated that subtle forms of ventricular fibrillation are apparent by observation of Normalized Curvature Difference Functions at specific instances of systole.

Each normalized curvature difference function is formed by differentially combining normalized curvature values from mid systolic outlines with corresponding normalized curvature values at end diastole. This differential combining for mid systolic normalized curvature difference functions is performed in an identical manner to the differential combining of end systolic and end diastolic values in FIG. 5A.

Based on clinical tests it was discovered that the normalized curvature difference is a quantitative measure of continuous geometric changes that occur in the left ventricle during systole. It was also discovered that numerical values obtained from the normalized curvature difference functions may be used to diagnose contraction abnormalities in the apical region, the inferior wall region and anterior wall region of the left ventricle at specific intervals of time during systole. It was discovered that the normalized curvature differences have definite properties which are characteristic of a normally contracting left ventricle.

Figure 6:
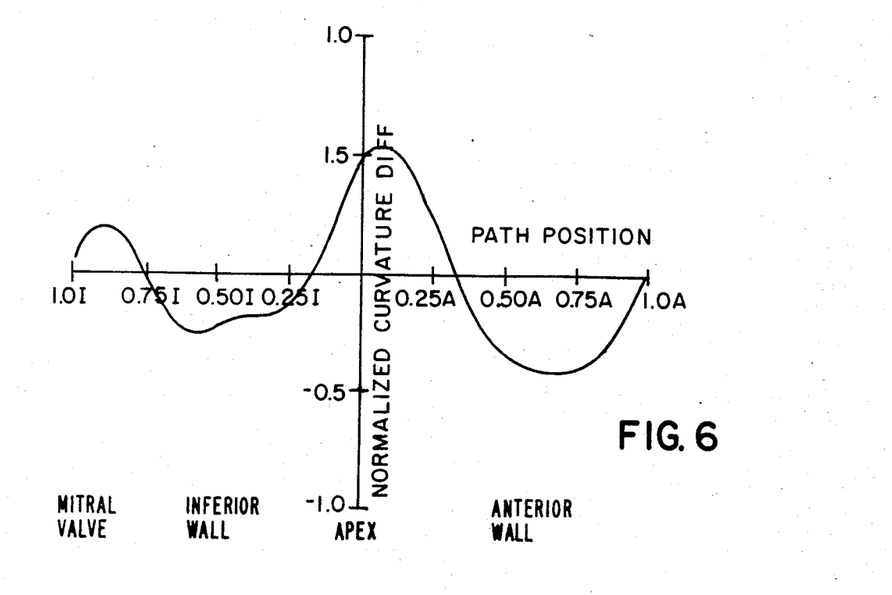
FIG. 6 is a graphical representation of the normalized curvature difference between end diastolic and end systolic outlines over the inferior wall, apical, and anterior wall regions based on the average of 58 Normal patients.

Referring to FIG. 6, there is shown a graphical representation of the average normalized curvature difference obtained from end diastolic and end systolic outlines over the inferior wall, apical, and anterior wall regions based on graphical representations of 58 normal patients. Based on a comparison of the graphical representation of average normal normalized curvature difference of FIG. 6 with the normalized curvature differences obtained from the end diastole and end systoleimages of 30 patients who were diagnosed to have contraction abnormality, the following information was discovered.

(1) A normal heart beat has a negative average value for the normalized curvature difference averaged over the inferior wall region at all instances of systole.

(2) A normal heart beat has a negative average value for the normalized curvature difference averaged over the anterior wall region at all instances of systole.

(3) A normal heart beat has a positive average value for the normalized curvature difference over the apical region at all instances of systole.

(4) Large fluctuations of the end diastolic/end systolic normalized curvature difference from the average normalized curvature difference of FIG. 6 indicates local contraction abnormality in the corresponding region. This fluctuation from the average normal may be used as a quantitative measure of local contraction abnormality.

It is expected that additional properties helpful in the diagnosis of contraction abnormality including valve abnormalities may be realized by similar examination of the normalized curvature difference between points which are located in teh valve region of the left ventricle.

Figure 7:
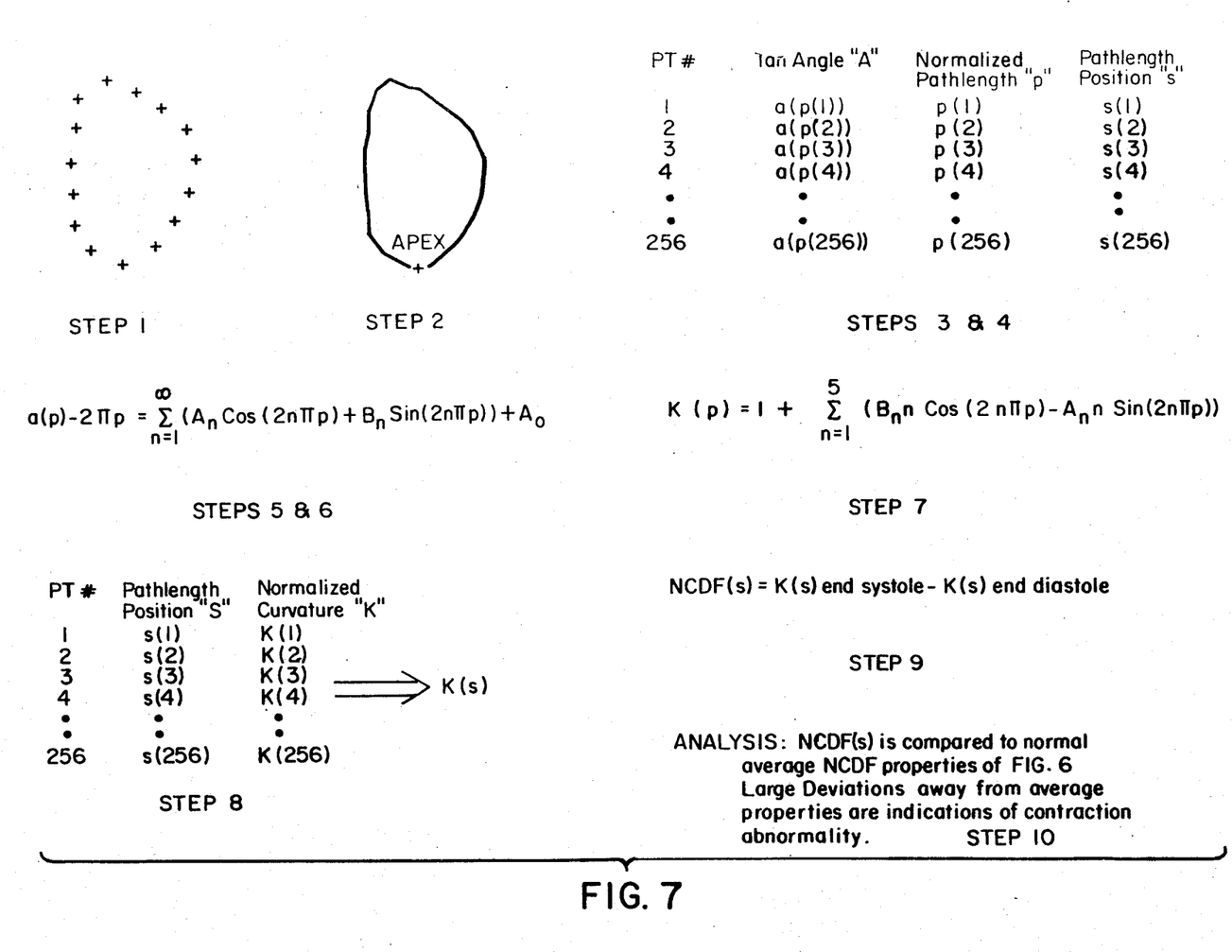
FIG. 7 is a chart setting forth steps in an exemplary embodiment of the invention.

Having described basic principles of the invention and its advantageous properties in characterizing shape and shape changes, the details of the process for determining the Normalized Curvature Difference Function (NCDF) will be described. Prior to performing the numbered steps described below, obtain a two dimensional long axis view image of the heart to be evaluated at end diastole, end systole, and mid systole by X-ray, ultrasonic or other suitable medical imaging techniques. Referring to FIG. 7, there is a chart of these steps in which the tangential angle is designated "a", the normalized pathlength is designated "p", and the pathlength position is designated "s".

Step 1: The X-Y coordinates of points on the end diastolic, end systolic and mid systolic outlines are recorded.

Step 2: Continuous end diastolic, end systolic and mid systolic outlines are formed by a spline fit of the points which were recorded for each outline in Step 1. The points which were originally recorded for each outline are connected by a cubic spline. The new spline fit outlines are numerically recorded by defining 256 closely spaced points on each of the new outlines. Thus the X-Y coordinates of 256 points are recorded for the cubic spline fit of the end diastolic outline, and the X-Y coordinates of 256 points are recorded for the spline fit of the end systolic and mid systolic outlines. One of these points is chosen as the apex of the heart for each outline. Thus an apex point is chosen for the end diastolic outline and an apex point is chosen for each of the end systolic and mid systolic outlines at the tip of the narrow end of each outline.

Step 3: Each of the 256 points on each outline is assigned a value for a tangential angle "a" and a normalized pathlength "p". The tangential angle at a point is defined as the angle of the line segment in the X-Y plane between that point and the next point on the shape in a counterclockwise direction. The normalized pathlength at a point is the fraction of perimeter distance measured to that point along the outline from the apex. The value of normalized pathlength varies from "0", where the path begins at the apex, to a value of unity, as the path closes on itself upon return to the apex.

Step 4: A value of pathlength position "s" is assigned to each point located on the anterior wall and inferior wall segments of the ventricle. The apex is assigned a pathlength position s=0. As the path is traversed in a clockwise direction from the apex, the entire inferior wall segment is defined as all points embraced between the apex and the intersection of the mitral valve with the aorta. Each point on this inferior wall segment is assigned a pathlength position value "s" corresponding to the fraction of the entire segment length consumed by the distance to the point measured along the path in a clockwise direction from the apex. Thus at the apex, s=0 and as the path is traversed in a clockwise direction the value of s increases until s=1.0 I at the very end of the segment. As the path is traversed in a counterclockwise direction from the apex, the anterior wall segment is defined as all points embraced between the apex and the intersection of the anterior wall with the aorta. Each point on this anterior wall segment is assigned a pathlength position "s" corresponding to the fraction of the entire segment length consumed by the distance to the point as measured along the path in a counterclockwise direction from the apex. Thus at the apex, s=0 and as the path is traversed in a counterclockwise direction, the value of s increases until s=1.0 A at the very end of the anterior wall segment.

Step 5: The 256 values of tangential angle "a" and normalized pathlength "p" recorded in step 3 for points on the end diastolic, end systolic and mid systolic outlines are processed as follows. For each point, subtract the normalized pathlength "p" multiplied by $2\pi$ from the tangential angle "a" in radians.

$$\text{value} = a - 2\pi p$$

By making this determination for each point on the normalized curvature, a new function $a(p) - 2\pi p$ is defined for each outline over the interval $0 \leq p \leq 1$.

Step 6: The function $a(p) - 2\pi p$ is expanded in a Fourier Series over the interval $0 \leq p \leq 1$ for each outline. Such a Fourier Series expansion is noted as follows:

$$a(p) - 2\pi p = A_o + \Sigma(A_n \cos(2\pi np) + B_n \sin(2\pi np)),$$
$$0 \leq p \leq 1.$$

where the Fourier Coefficients $A_o$, $A_n$, $B_n$ are determined according to the standard techniques of Fourier Analysis. A set of coefficients is thus obtained by Fourier Analysis of each outline.

Step 7: The first five harmonics of the Fourier Coefficients from Step 6 are used to determine the normalized curvature "K" as a function of normalized pathlength "p". The determination of normalized curvature K(p) over the interval $0 \leq p \leq 1$ is accomplished with the Fourier coefficients $A_n$, $B_n$ ($1 \leq n \leq 5$) of Step 6 according to the following formula:

$$K(p) = 1 + \Sigma\{nB_n \cos(2\pi np) - nA_n \sin(2\pi np)\},$$
$$0 \leq p \leq 1.$$

Step 8: A Normalized Curvature Distribution K(s) is determined by retrieving for each point on anterior and inferior wall segments the value of normalized curvature "k" as determined in Step 7 and the value of pathlength position "s" as determined in Step 4. A function k(s) which is normalized curvature vs. pathlength position is thus formed for each outline over the pathlength position intervals $0 \leq s \leq 1.0$ I (of the inferior wall) and $0 \leq s \leq 1.0$ A (of the anterior wall). The function K(s) is called the Normalized Curvature Distribution of the outline. A Normalized Curvature Distribution is calculated for the end diastole outline and a Normalized Curvature Distribution is calculated for the end systole and mid systole outlines of the ventricle.

Step 9: Normalized Curvature Difference Functions NCDF are determined at each interval of systole over the pathlength position intervals $0 \leq s \leq 1.0$ I and $0 \leq s \leq 1.0$ A by subtraction of the end diastolic Normalized Curvature Distribution from the end systolic and mid systolic Normalized Curvature Distributions. end diastole/end systole $$NCDF(s) = K(s) - K(s) \quad 0 \leq s \leq 1.0I$$
$$\text{end systole} \quad \text{end diastole}$$

$$NCDF(s) = K(s) - K(s) \quad 0 \leq s \leq 1.0 \; A$$

diastole/mid systole / mid systole end diastole

In the terminology of this invention, the Normalized Curvature Difference Function is determined by the differential combining of normalized curvature between corresponding points of two shapes. It will be obvious to those skilled in the art that an infinite number of such point to point correspondences may be made and need not necessarily be restricted to points of common pathlength position "s" as defined in Step 4. Other point to point correspondences such as points of common normalized pathlength "p" may be employed to construct a Normalized Curvature Difference Function such as NCDF(p) where the normalized curvature difference would be expressed as a function of normalized pathlength "p" on the two shapes. Normalized curvature differences may also be determined for points of the left ventricle in the valve region (which are not assigned pathlength positions in Step 4) by employing an appropriate definition of point to point correspondences in the valve regions of two shapes.

Step 10: The Normalized Curvature Difference Functions are compared to average NCDF's obtained from a large population of normals such as shown in FIG. 6. Deviations of the NCDF away from the average normal NCDF at a particular location of the pathlength position is interpreted as a contraction abnormality at the region of the heart corresponding to that value of the pathlength position.

While the invention is especially advantageous in connection with evaluating cardiac conditions, the invention has general utility in characterizing and comparing other curves and outlines. While the invention may be practiced manually in making the determinations noted above, preferably the invention is practiced with a computer which may receive information through a keyboard or other input devices and provide the normalized curvature and/or normalized curvature difference functions on a screen, in tabular form, or in graphical form on hard copy. Specific programs for implementing the determinations described above may readily be prepared by those skilled in the art.

It is evident that those skilled in the art may now make numerous uses and modifications of and departures from the specific apparatus and techniques herein disclosed without departing from the inventive concepts. Consequently, the invention is to be construed as embracing each and every novel feature and novel combination of features present in or possessed by the apparatus and techniques herein disclosed and limited solely by the spirit and scope of the appended claims.

What is claimed is:

1. A method of characterizing the condition of a heart which method includes the steps of, medically imaging said heart to obtain the outline of the end diastole image as a first curve and the end systole outline image as a second curve, determining the normalized curvature of a sequence of points along each of said curves over a predetermined pathlength as a function of the normalized distance of a respective point along said pathlength, determining for each of said points the functional relationship of said normalized curvature to the normalized distance of the associated point along said pathlength to obtain first normalized curvature values of said first curve and second normalized curvature values of said second curve, and differentially combining said first normalized curvature values and said second normalized curvature values at corresponding values of position along said pathlengths to provide a difference functional relationship representative of the difference in shape between said first and second curves, said curves each defining a closed loop and each pathlength corresponding to a segment of a respective closed loop beginning and ending at predetermined reference points on said closed loops.

2. A method of characterizing the condition of a heart in accordance with claim 1 and further including the steps of providing a signal characteristic of said difference functional relationship for a normal heart for said end diastole image outline and said end systole image outline, and comparing the latter signal with the difference functional relationship representative of the difference between first and second curves corresponding to the outlines of the end systole and end diastole images respectively of said heart.

* * * * *